United States Patent [19]

Schambil et al.

[11] Patent Number: 6,086,787
[45] Date of Patent: Jul. 11, 2000

[54] PROCESS FOR THE PRODUCTION OF OIL-IN-WATER CREAMS

[75] Inventors: Fred Schambil, Monheim; Ulrich Zeidler, Duesseldorf; Soraya Shamsai, Cologne; Thomas Foerster, Erkrath; Holger Tesmann, Duesseldorf, all of Germany

[73] Assignee: Henkel Kommanditgesellschaft auf Aktien, Duesseldorf, Germany

[21] Appl. No.: 09/233,592

[22] Filed: Jan. 19, 1999

Related U.S. Application Data

[63] Continuation of application No. 07/927,289, filed as application No. PCT/EP91/00556, Mar. 21, 1991, abandoned.

[30] Foreign Application Priority Data

Mar. 30, 1990 [DE] Germany ............................. 40 10 393

[51] Int. Cl.$^7$ ..................................................... B01J 13/00
[52] U.S. Cl. ......................... 252/312; 424/401; 514/846; 514/938; 514/943
[58] Field of Search ........................... 252/312; 424/401; 514/846, 938, 943

[56] References Cited

U.S. PATENT DOCUMENTS

| | | | |
|---|---|---|---|
| 4,146,499 | 3/1979 | Rosano | 252/186.32 |
| 4,472,291 | 9/1984 | Rosano | 252/186.28 |
| 4,620,878 | 11/1986 | Gee | 106/287.15 |

FOREIGN PATENT DOCUMENTS

| | | | |
|---|---|---|---|
| 345586 A | 12/1986 | European Pat. Off. | |
| 89/11907 | 12/1989 | WIPO | |

OTHER PUBLICATIONS

Jellinek, J. S. Formulation and Function of Cosmetics. 1971. Substances Which Increase the Viscosity of the Aqueous Phase. pp. 146–152.

*Primary Examiner*—Robert H. Harrison
*Attorney, Agent, or Firm*—Ernest G. Szoke; Wayne C. Jaeschke; Henry E. Millson, Jr.

[57] ABSTRACT

Process for the preparation of oil-in-water creams comprising the steps of

I forming a low-viscosity, very fine particle oil-in-water emulsion by heating the following composition to a temperature within or above its phase inversion temperature range:
  A) 1 part by weight of liquid oil component,
  B) from about 0.1 to about 0.5 parts by weight of at least one nonionic emulsifier having an HLB value of from 11 to 15,
  C) from about 0.1 to about 0.2 parts by weight of at least one co-emulsifier selected from saturated fatty alcohols containing 16 to 22 carbon atoms and partial esters of polyols containing 3 to 6 carbon atoms with saturated fatty acids containing 143 to 22 carbon atoms, and
  D) from about 1 to about 6 parts by weight of water; and II thickening the emulsion from step I to the consistency of a cream by adding thereto at least one consistency generator selected from co-emulsifiers defined in step I C) above and water-soluble polymers, wherein the thickened emulsion exhibits plastic behavior at 20° C. with a yield point of at least about 5 Pascal.

22 Claims, No Drawings

PROCESS FOR THE PRODUCTION OF OIL-IN-WATER CREAMS

CROSS REFERENCE TO RELATED APPLICATIONS

This application is a continuation of U.S. application Ser. No. 07/927,289, Sep. 30, 1992, now abandoned, which is a 371 of PCT/EP91/00556, filed on Mar. 21, 1991.

This invention relates to a process for the production of creams of the oil-in-water emulsion type.

It is known that oil-in-water emulsions prepared with nonionic emulsifiers undergo phase inversion on heating, i.e. the outer aqueous phase can become the inner phase at relatively high temperatures. This process is generaly reversible, so that the original emulsion type is reformed on cooling. In "Progress in Colloid & Polymer Science" 73, (1987), 37–47, F. Schambil, F. Jost and M. J. Schwuger report on properties of cosmetic emulsions of paraffin oil and paraffin oil/ester oil mixtures and also mention the fact that emulsions prepared above the phase inversion temperature have a lower viscosity and higher stability in storage.

DE-A-38 19 193 describes liquid-oil-in water emulsions of polar oil components which are prepared at a temperature in or beyond the phase inversion temperature range and which are therefore low-viscosity, fine-particle and very stable emulsions. Where specially selected emulsifiers and co-emulsifiers are used, the emulsions in question are so fine that their particles are no longer optically visible. Emulsions such as these, which have a transparent, bluish opalescent appearance, are also known as microemulsions.

Although high particle fineness and stability are desirable for cosmetic purposes, cosmetic emulsions at the same time should not be free-flowing, but should have an ointment-like or creamy consistency for a number of applications. In the conventional production of creams, this was achieved by increasing the percentage content of the inner phase (oil component), by using solids fats or waxes or by using soaps or other thickening or gel-forming anionic emulsifiers. The measures mentioned added considerably to the cost of the emulsion systems or reduced the fineness and stability of the emulsions and impaired their dermatological compatibility or the cosmetic feeling of the skin.

It has now been found that creams of the oil-in-water type can be produced with considerable advantage from liquid oil components by initially preparing a low-viscosity, very fine-particle oil-in-water emulsion in known manner with phase inversion and subsequently thickening the emulsion by consistency-generating co-emulsifiers or thickening hydrophilic polymers.

Accordingly, the present invention relates to a process for the production of oil-in-water creams from liquid oil components by conversion of (A) 1 part by weight of the oil component with (B) 0.1 to 0.5 part by weight of a nonionic emulsifier having an HLB value of 11 to 15 and (C) 0.1 to 0.2 part by weight of a co-emulsifier from the group of saturated fatty alcohols containing 16 to 22 carbon atoms or partial esters of polyols containing 3 to 6 carbon atoms with saturated fatty acids containing 14 to 22 carbon atoms and (D) 1 to 6 parts by weight water into a low-viscosity, very fine-particle oil-in-water emulsion at a temperature above or within the phase inversion temperature range and subsequent thickening of the emulsion thus formed to the consistency of a cream by introduction of a lipophilic consistency generator selected from the co-emulsifiers mentioned in (C) or of a water-soluble polymer.

The lipophilic consistency generator may be introduced both above and within or below the phase inversion temperature range.

The oil-in-water creams obtained by the process according to the invention are distinguished by particularly high particle fineness and stability coupled with a very good, cosmetically desirable cream consistency and spreadability.

In the context of the invention, the expression "cream consistency" is understood to be a rheological state in which the emulsion shows plastic behavior at room temperature (20° C.) with a yield point of at least 5 Pascal [Pa] and preferably in the range from 10 to 50 Pascal.

Suitable oil components are any water-insoluble, branched or linear, physiologically safe hydrocarbons, ethers or esters and fatty oils (triglycerides) which are liquid at room temperature (20° C.). However, it is also possible to use solid or relatively high-melting paraffins, esters, waxes or fats in such quantities that the mixture containing the liquid oil components remains liquid at 20° C.

Preferred oil components are paraffin oils and synthetic hydrocarbons, for example liquid polyolefins, or defined hydrocarbons, for example alkyl cyclohexanes, such as 1,3-diisooctyl cyclohexane for example.

However, other suitable oil components are monoesters and diesters corresponding to the formulae

$$R^1COOR^2 \tag{I}$$

$$R^2\text{—OOC—R—COOR}^2 \tag{II}$$

$$R^1\text{—COO—R}^3\text{—OOC—R}^1 \tag{III}$$

in which $R^1$ and $R^2$ are $C_{1-22}$ alkyl groups or $C_{8-22}$ alkenyl groups and $R^3$ represents $C_{2-16}$ alkylene groups, which contain at least 10 carbon atoms and/or fatty acid triglycerides of fatty acids containing 8 to 22 carbon atoms.

Oil components selected from the monoesters and diesters corresponding to formulae I, II and III are known as cosmetic and pharmaceutical oil components and as components of lubricants and greases. Among monoesters and diesters of this type, the greatest significance is attributed to the products which are liquid at room temperature (20° C.). Monoesters (I) suitable as oil components are, for example, the methyl esters and isopropyl esters of $C_{12-22}$ fatty acids such as, for example, methyl laurate, methyl stearate, methyl oleate, methyl erucate, isopropyl palmitate, isopropyl myristate, isopropyl palmitate, isopropyl stearate and isopropyl oleate. Other suitable monoesters are, for example, n-butyl stearate, n-hexyl laurate, n-decyl oleate, isooctyl stearate, isononyl palmitate, isononyl isononanoate, 2-ethylhexyl palmitate, 2-ethylhexyl laurate, 2-hexyldecyl stearate, 2-octyl dodecyl palmitate, oleyl oleate, oleyl erucate, erucyl oleate and esters obtainable from technical aliphatic alcohol mixtures and technical aliphatic carboxylic acids, for example esters of saturated and unsaturated $C_{12-22}$ fatty alcohols and saturated and unsaturated $C_{12-22}$ fatty acids of the type obtainable from animal and vegetable fats. Naturally occurring monoesters or wax ester mixtures, for example of the type present in jojoba oil or in sperm oil, are also suitable.

Suitable dicarboxylic acids (II) are, for example, di-n-butyl adipate, di-n-butyl sebacate, di-(2-ethylhexyl)-adipate, di-(2-hexyldecyl)-succinate and diisotridecyl azelate. Suitable diol esters (III) are, for example, ethylene glycol dioleate, ethylene glycol diisotridecanoate, propylene glycol di-(2-ethylhexanoate), butanediol diisostearate and neopentyl glycol dicaprylate.

Suitable fatty acid diglycerides are natural vegetable oils, for example olive oil, sunflower oil, soybean oil, peanut oil, rapeseed oil, almond oil, palm oil, and also the liquid components of coconut oil or palm kernel oil, and animal oils such as, for example, neat's foot oil, the liquid components of beef tallow, or even synthetic triglycerides of the type obtained by esterification of glycerol with $C_{8-22}$ fatty acids, for example triglycerides of caprylic acid/capric acid mixtures, triglycerides of technical oleic acid or of palmitic acid mixtures.

Nonionic emulsifiers suitable as emulsifiers (B) are characterized by a lipophilic, preferably linear, alkyl or acyl group and by a hydrophilic group formed from low molecular weight glycol, glucose and polyol ethers.

Nonionic ethylene oxide adducts with $C_{16-22}$ fatty alcohols suitable as emulsifiers (B) are commercially available products. The technical products are mixtures of homologous polyglycol ethers of the starting fatty alcohols of which the average degree of ethoxylation corresponds to the mols of ethylene oxide added on. Ethylene oxide adducts with partial esters of a $C_{3-6}$ polyol and $C_{14-22}$ fatty acids may also be used as emulsifiers. Products such as these may be prepared, for example, by ethoxylation of glycerol monostearate, glycerol monopalmitate or mono- and difatty acid esters of sorbitan, for example sorbitan monostearate or sorbitan sesquioleate. The emulsifiers suitable for the process according to the invention should have an HLB value of 11 to 15. The HLB value (hydrophilic/lipophilic balance) is a value which may be calculated in accordance with the following equation $$HLB = \frac{100 - L}{5}$$

where L is the quantity by weight of the lipophilic groups, i.e. the fatty alkyl or fatty acyl groups, in % by weight in the ethylene oxide adducts.

In addition to the emulsifier, a co-emulsifier (C) is necessary for the production of the oil-in-water emulsions by the process according to the invention. On account of its hydrophilic character, the co-emulsifier itself is not suitable for the preparation of oil-in-water emulsions, although particularly stable and fine emulsions of the polar oil components can be prepared with the emulsifiers defined above. According to the invention, suitable co-emulsifiers are those of the saturated $C_{16-22}$ fatty alcohol type, for example cetyl alcohol, stearyl alcohol, arachidyl alcohol or behenyl alcohol or mixtures of these alcohols of the type obtained in the industrial hydrogenation of vegetable and animal $C_{16-22}$ fatty acids or corresponding fatty acid methyl esters. Other suitable co-emulsifiers are partial esters of a $C_{3-6}$ polyol and saturated and/or unsaturated $C_{14-22}$ fatty acids. Partial esters such as these are, for example, the monoglycerides of palmitic acid, stearic acid and oleic acid, the sorbitan monoesters and/or diesters of myristic acid, palmitic acid, stearic acid or mixtures of these fatty acids, the monoesters of trimethylol propane, erythritol or pentaerythritol and saturated fatty acids containing 14 to 22 carbon atoms. Monoesters are also understood to be the technical monoesters which are obtained by esterification of 1 mol polyol with 1 mol fatty acid and which represent a mixture of monoester, diester, triester and, optionally, non-esterified polyol.

In a particularly preferred embodiment, an emulsion which is so fine that the emulsion droplets are sub-microscopically fine and the emulsion has a transparent, bluish opalescent appearance is initially formed in the process according to the invention. Emulsions such as these are also known as microemulsions. Microemulsions are obtained when the type and quantities of oil components, emulsifiers and co-emulsifiers are coordinated with one another in the preferred manner. For example, the oil component (A) preferably consists of 50 to 100% by weight of a hydrocarbon oil and 0 to 25% by weight of a monoester or diester corresponding to formulae I, II or III and 0 to 25% of a fatty acid triglyceride of $C_{8-22}$ fatty acids.

Adducts of 8 to 16 mol ethylene oxide with saturated $C_{16-22}$ fatty alcohols are preferably used as the nonionic emulsifiers (B). If a polar oil component, for example an ester corresponding to formula I, II or III or a triglyceride is used, it is particularly preferred to use an adduct of 8 to 15 mol ethylene oxide with a saturated, linear $C_{20-22}$ fatty alcohol as emulsifier.

The process according to the invention may be carried out by initially determining the phase inversion temperature by heating a sample of the emulsion prepared in the usual way using a conductivity measuring instrument and determining the temperature at which the conductivity undergoes a pronounced reduction. The specific conductivity of the oil-in-water emulsion initially present normally decreases from, initially, more than 1 millisiemens per cm (mS/cm) to values below 0.1 mS/cm over a temperature range of 2 to 8° C. This temperature range is referred to herein as the phase inversion temperature range.

Once the phase inversion temperature range is known, the process according to the invention may be carried out either by subsequently heating the emulsion initially prepared in the usual manner to a temperature lying in or beyond the phase inversion temperature range or by actually preparing the emulsion at a temperature lying in or beyond the phase inversion temperature range.

Subsequent thickening is preferably carried out by incorporation of 0.01 to 0.3 part by weight (per part by weight of the oil component) of a lipophilic consistency generator in the liquid, fine-particle emulsion or microemulsion. To this end, the consistency generator is heated beyond its melting point and intensively mixed with the emulsion heated to the same temperature which may even lie in the phase inversion temperature range. After cooling to room temperature (20° C.), a non-flowing cream is formed.

Suitable lipophilic consistency generators are any products of the type described above as co-emulsifers (C). Preferred lipophilic consistency generators are linear saturated fatty alcohols containing 16 to 22 carbon atoms, more particularly cetyl alcohol and stearyl alcohol and also glycerol monostearate and mixtures of glycerol monostearate and distearate.

Subsequent thickening by introduction of a water-soluble polymer is preferably carried out by adding an aqueous solution of 0.005 to 0.1 part by weight of a water-soluble polymer (per part by weight of the oil component) to the liquid fine-particle emulsion or microemulsion. Suitable water-soluble thickening polymers are any water-soluble polymers having a molecular weight in the range from 500,000 to 5,000,000. Suitable polymers are natural substances such as, for example, vegetable gums, guar, soluble starch or biopolymers such as, for example, xanthan gum or even water-soluble derivatives of such natural products such as, for example, carboxymethyl starch, hydroxyethyl cellulose, hydroxypropyl guar, etc.

Other suitable polymers are water-soluble synthetic polymers such as, for example, polyvinyl pyrrolidone, polyvinyl alcohol, polyethylene oxides, polyacrylamides and also polymers and copolymers of acrylic acid and methacrylic acid.

Crosslinked acrylic acid polymers or copolymers having an average molecular weight in the range from 500,000 to 5,000,000 in the form of the water-soluble salts and also water-soluble nonionic cellulose ethers or mixtures thereof have proved to be particularly suitable.

Suitable water-soluble nonionic cellulose ethers are, for example, methyl cellulose, hydroxyethyl cellulose, hydroxypropyl cellulose and/or methyl hydroxypropyl celluloses. Hydroxypropyl cellulose and methyl hydroxypropyl cellulose are particularly suitable. Hydroxypropyl celluloses are commercially obtainable, for example, under the trademark KLUCEL® (Hercules) while methyl hydroxypropyl celluloses are commercially obtainable under the trademark BENECEL®MO (Aqualon GmbH & Co. KG).

The various commercial types of these nonionic cellulose ethers differ in the degree of substitution and the degree of degradation of the cellulose (i.e. the average molecular weight), qualities varying in their solution viscosity being obtained.

Suitable methyl hydroxypropyl celluloses have a viscosity in the form of 2% by weight aqueous solutions at 20° C. of 40 to 40,000 mpas, as measured with a Brookfield rotational viscosimeter at 20 r.p.m.

Suitable crosslinked acrylic acid polymers are products obtained by copolymerization of acrylic acid with, for example, 0.1 to 4.0% by weight of a polyalkylene polyether of a polyhydric alcohol containing more than one alkenyl ether group per molecule as crosslinking agent. One example of such a crosslinking agent is polyallyl sucrose.

Other comonomers may optionally be used in quantities of up to 59% by weight of the monomer mixture in the production of the crosslinked acrylic acid polymers. Suitable comonomers are, for example, maleic anhydride, N-methyl acrylamide, methyl vinyl ether or mixtures of these additional monomers. Crosslinked acrylic acid polymers of the type in question are known, for example, from U.S. Pat. No. 2,798,053 and are commercially available under the trademark CARBOPOL® (Goodrich). The crosslinked acrylic acid polymers may be dispersed in water, although the strong thickening effect is only achieved when the polymers are converted into the salt form by inorganic bases such as, for example, sodium hydroxide, potassium hydroxide, ammonia or by low molecular weight amines or alkanolamines.

In the form of 1% by weight aqueous solutions neutralized with sodium hydroxide to a pH value of 7 to 8 at 20° C., suitable acrylic acid polymers have a viscosity of 1,000 to 100,000 mpas, as measured with a Brookfield rotational viscosimeter at 20 r.p.m.

Addition of the aqueous solution or swelling of the polymer and mixing with the fine-particle liquid emulsion or microemulsion prepared beforehand is best carried out by heating both the polymer solution and the emulsion to a mixing temperature of 30 to 80° C. and then mixing and homogenizing them with intensive stirring, optionally using static or dynamic mixing or emulsifying units. The mixing temperature selected is so high that the thickened emulsion formed still remains free-flowing. After cooling to room temperature (20° C.), the thickened emulsion then solidifies to form the non-flowing plastic cream.

A particularly good thickening effect is also obtained by using both a lipophilic consistency generator and a water-soluble polymer for thickening.

The following Examples are intended to illustrate the invention without limiting it in any way.

EXAMPLES

1. Production of the Emulsions (Standard Procedure)

The oil components, emulsifiers and co-emulsifiers were mixed and the resulting mixture was heated to a temperature below its melting point and homogenized. The melt was then emulsified with stirring into the water which had been heated to substantially the same temperature. The composition of the emulsions is shown in Table 1.

2. Determination of the Phase Inversion Temperature

Using a conductivity measuring bridge (manufacturer: Radiometer, Copenhagen), the electrical conductivity of the emulsions was measured as a function of the temperature. To this end, the emulsion was first cooled to +20° C. At this temperature, the emulsions showed a conductivity of more than 1 millisiemens per cm (mS/cm), i.e. they were oil-in-water emulsions. A conductivity curve was then established by slow heating at a rate of approx. 0.5° C./min. which was controlled by means of a temperature programmer in conjunction with a cryostat. The temperature range in which the conductivity fell to a value below 0.1 mS/cm was recorded as the phase inversion temperature range. With all the emulsions listed in Table I, this temperature range was below 100° C. (Table I, phase inversion).

3. Production of the Emulsions in Accordance With the Invention

The emulsions were prepared as described in 1. and were then briefly heated (for about 1 minute) to a temperature in or slightly above the phase inversion temperature range (95° C. in all Examples). The emulsions were then rapidly cooled, i.e. at a rate of approx. 2° C. per minute, with stirring to room temperature. After 24 hours, their fluidity and yield point were determined. All the microemulsions prepared in accordance with Table I, Examples 1.1 to 1.8, were liquid, i.e. moved under the effect of gravity. The yield point was well below 0.1 Pa (20° C.).

4. Preparation of the Creams in Accordance With the Invention

Creams 2.1 to 2.8 were prepared from microemulsions 1.1 to 1.8 by addition of the consistency generators listed in Table I in the quantities indicated and at the mixing temperature indicated.

To this end, the consistency generator (C) was heated to the mixing temperature in Examples 2.1 to 2.6. The microemulsion which had been heated to the same temperature was then added with intensive stirring. In Examples 2.7 and 2.8, the polymer solution heated to the mixing temperature was mixed with the microemulsion which had been heated to the same temperature. After cooling to 20° C., creams were formed which did not show any fluidity under the effect of gravity.

After storage for 24 hours at 20° C., the yield point [Pa] was measured in a rotational viscosimeter (Carrimed Controlled Stress Rheometer).

TABLE I

| Microemulsion No. | C | 1.1 | 1.2 | 1.3 | 1.4 | 1.5 | 1.6 | 1.7 | 1.8 | 1.9 | 1.10 | 1.11 |
|---|---|---|---|---|---|---|---|---|---|---|---|---|
| Paraffin oil (DAB6), thickly liquid (% by weight) | 20 | 20 | 20 | 20 | 20 | 20 | 15 | 20 | 20 | 20 | 20 | 20 |
| Decyl oleate (% by weight) | | | | | | | 5 | | | | | |
| Cetyl/stearate alc.$^{c)}$ + 12 EO (% by weight) | 4 | 4 | 4 | 4 | 4 | 4 | 4 | 4 | 4 | 4 | 4 | 4 |
| Cetyl/stearyl alc.$^{c)}$ (% by weight) | 3 | 3 | 3 | 3 | 3 | 3 | — | 3 | | | 3 | 3 |
| Glycerol mono-/distearate (% by weight) | $2^{a)}$ | | | | | | $3^{a)}$ | | $3^{b)}$ | $3^{b)}$ | | |
| Water (% by weight) | 71 | 73 | 73 | 73 | 73 | 73 | 73 | 73 | 73 | 73 | 73 | 73 |
| Phase invention [° C.] | — | 81–91 | 81–91 | 81–91 | 81–91 | 81–91 | 69–77 | 81–89 | 65–74 | 65–74 | 81–89 | 81–89 |
| Yield point 20° C. [Pa] | 1.3 | Under 0.1 [Pa], thinly liquid microemulsion | | | | | | | | | | |

Legend to Table I:
$^{a)}$The quantities of glycerol mono-/distearate identified by the index $^{a)}$consisted of a technical partial glyceride of a palmitic/stearic acid mixture (30:70) containing 50% by weight monoglyceride, 40% by weight diglyceride and 10% by weight triglyceride.
$^{b)}$The quantities of glycerol mono-/distearate identified by the index $^{b)}$consisted of a technical partial glyceride of a palmitic/stearic acid mixture (50:50) containing 42% by weight monoglyceride, 38% by weight diglyceride and 20% by weight triglyceride.
$^{c)}$The cetyl/stearyl alcohol mixture identified by the index $^{c)}$consisted of approx. 50% by weight cetyl alcohol and 50% by weight stearyl alcohol.

TABLE II

| Thickening: | | | Cream No. | | | | | | | | | | |
|---|---|---|---|---|---|---|---|---|---|---|---|---|---|
| | | | 2.1 | 2.2 | 2.3 | 2.4 | 2.5 | 2.6 | 2.7 | 2.8 | 2.9 | 2.10 | 2.11 |
| Microemulsion | No. | C | 1.1 | 1.2 | 1.3 | 1.4 | 1.5 | 1.6 | 1.7 | 1.8 | 1.9 | 1.10 | 1.11 |
| | % by weight | | 98 | 98 | 95.5 | 96 | 96 | 96 | 98 | 90 | 90 | 85 | 90 |
| Cetyl/stearyl alc.$^{c)}$ (% by weight) | | | | 2 | — | 4 | 4 | 4 | | | | | |
| Glycerol mono-/distearate (% by weight) | | | $2^{a)}$ | | $2^{a)}$ | | | | $2^{a)}$ | $10^{b)}$ | $10^{b)}$ | | |
| Carbopol ® 940 solution (2% in H$_2$O/KOH) | | | | | 2.5 | | | | | | | 15 | 10 |
| Mixing temperature (° C.) | | 75 | 75 | 70 | 70 | 65 | 96 | 70 | 75 | 65 | 80 | 60 | 95 |
| Yield point 20° C. [Pa] | | 1.3 | 11 | 14 | 22 | 27 | >15 | 16 | 11 | 14 | 36 | 43 | 9 |

We claim:

1. A process for the preparation of an oil-in-water cream comprising the steps of
   I) forming an oil-in-water emulsion by heating the following composition to a temperature within or above its phase inversion temperature range:
      A) 1 part by weight of a physiologically safe liquid oil component,
      B) from about 0.1 to about 0.5 parts by weight of at least one nonionic emulsifier having an HLB value of from 11 to 15,
      C) from about 0.1 to about 0.2 parts by weight of at least one co-emulsifier selected from the group consisting of saturated fatty alcohols containing 16 to 22 carbon atoms and partial esters of polyols containing 3 to 6 carbon atoms with saturated fatty acids containing 14 to 22 carbon atoms, and
      D) from about 1 to about 6 parts by weight of water; and
   II) thickening the emulsion from Step I to the consistency of a cream by
      A) heating an aqueous solution of a water soluble polymer to a temperature of from about 30 to about 80° C.,
      B) heating the emulsion formed in Step I to a temperature of from about 30 to about 80° C.,
      C) mixing together the heated aqueous solution from step II A) and the heated emulsion from step II B) and homogenizing the resulting mixture with intensive stirring to produce a thickened emulsion which remains free-flowing until cooled to room temperature, and
      D) cooling the free-flowing thickened emulsion to room temperature to produce a non-flowing plastic cream with a yield point of at least about 5 Pascal.

2. The process of claim 1 wherein a lipophilic consistency generator is also added in step II.

3. The process of claim 1 wherein a lipophilic consistency generator which is the co-emulsifier set forth in step I C) of claim 1 is also added in step II.

4. The process of claim 1 wherein in step II D) the thickened emulsion has a yield point of from about 20 to about 50 Pascal.

5. The process of claim 1 wherein in step II A) the water-soluble polymer is present in the form of an aqueous solution of from about 0.005 to about 0.1 part by weight of a water-soluble polymer having a number average molecular weight in the range of from 500,000 to 5,000,000, wherein the parts by weight of water-soluble polymer are based on component I A).

6. The process of claim 5 wherein the water-soluble polymer is selected from the group consisting of crosslinked acrylic acid polymers or copolymers having a number average molecular weight in the range of from about 500,000 to about 5,000,000 in the form of their water-soluble salts, and at least one water-soluble, nonionic cellulose ether.

7. The process of claim 3 wherein in step II from about 0.01 to about 0.3 parts by weight of a co-emulsifier as set forth in step I C) is added.

8. The process of claim 1 wherein the nonionic emulsifier in step I B) is an adduct of 8 to 16 mols of ethylene oxide with a saturated $C_{16-22}$ fatty alcohol.

9. The process of claim 1 wherein in step I A) the liquid oil component consists of from about 50 to 100% by weight of a hydrocarbon oil, from 0 to about 25% by weight of at least one ester of the formulae $$R^1COOR^2$$

$$R^2\text{---}OOC\text{---}R^3\text{---}COOR^2$$

$$R^1\text{---}COO\text{---}R^3\text{---}OOC\text{---}R^1$$

in which $R^1$ and $R^2$ are $C_{1-22}$ alkyl groups or $C_{8-22}$ alkenyl groups and $R^3$ is a $C_{2-16}$ alkylene group, and wherein the ester contains at least 10 carbon atoms, and from 0 to about 25% by weight of a fatty acid triglyceride of $C_{8-22}$ fatty acids.

10. The process of claim 1 wherein the oil-in-water emulsion formed in step I A) is a microemulsion.

11. The process of claim 1 wherein in step I A) the liquid oil component consists of from about 50 to 100% by weight of a hydrocarbon oil, from 0 to about 25% by weight of at least one ester of the formulae $$R^1COOR^2$$

$$R^2\text{---}OOC\text{---}R^3\text{---}COOR^2$$

$$R^1\text{---}COO\text{---}R^3\text{---}OOC\text{---}R^1$$

in which $R^1$ and $R^2$ are $C_{1-22}$ alkyl groups or $C_{8-22}$ alkenyl groups and $R^3$ is a $C_{2-16}$ alkylene group, and wherein the ester contains at least 10 carbon atoms, and from 0 to about 25% by weight of a fatty acid triglyceride of $C_{8-22}$ fatty acid; the nonionic emulsifier in step I B) is an adduct of 8 to 16 mols of ethylene oxide with a saturated C,6-22 fatty alcohol; and in step II D) the thickened emulsion has a yield point of from about 10 to about 50 Pascal.

12. The process of claim 2 wherein in step II the lipophilic consistency generator is selected from the group consisting of cetyl alcohol, stearyl alcohol, glycerol monostearate, and mixtures of glycerol mono- and distearate.

13. A process for the preparation of an oil-in-water cream comprising the steps of I) forming an oil-in-water emulsion by heating the following composition to a temperature within or above its phase inversion temperature range;
   A) 1 part by weight of a physiologically safe liquid oil component,
   B) from about 0.1 to about 0.5 parts by weight of at least one nonionic emulsifier having an HLB value of from 11 to 15,
   C) from about 0.5 to about 0.2 parts by weight of at least one co-emulsifier selected from the group consisting of saturated fatty alcohols containing 16 to 22 carbon atoms and partial esters of polyols containing 3 to 6 carbon atoms with saturated fatty acids containing 14 to 22 carbon atoms, and
   D) from about 1 to about 6 parts by weight of water; and II thickening the emulsion from step I to the consistency of a cream by A) heating a lipophilic consistency generator selected from the group consisting of saturated fatty alcohols containing 16 to 22 carbon atoms and partial esters of polyols containing 3 to 6 carbon atoms with saturated fatty acids containing 14 to 22 carbon atoms, to a temperature beyond its melting point,
B) heating the emulsion from step I to about the same temperature as the heated consistency generator,
C) intensively mixing together the heated consistency generator from step II A) and the heated emulsion from step II B), and
D) cooling the resulting mixture to room temperature to form a non-flowing cream.

14. The process of claim 13 wherein in step II D) the thickened emulsion has a yield point of from about 20 to about 50 Pascal.

15. The process of claim 13 wherein in step II C) about 0.01 to about 0.3 parts by weight of the consistency generator is present therein.

16. The process of claim 13 wherein the nonionic emulsifier in step I B) is an adduct of 8 to 16 mols of ethylene oxide with a saturated $C_{16-22}$ fatty alcohol.

17. The process of claim 13 wherein in step I A) the liquid oil component consists of from about 50 to 100% by weight of a hydrocarbon oil, from 0 to about 25% by weight of at least one ester of the formulae $$R^1COOR^2$$

$$R^2\text{---}OOC\text{---}R^3\text{---}COOR^2$$

$$R^1\text{---}COO\text{---}R^3\text{---}OOC\text{---}R^1$$

in which $R^1$ and $R^2$ are $C_{1-22}$ alkyl groups or $C_{8-22}$ alkenyl groups and $R^3$ is a $C_{2-16}$ alkylene group, and wherein the ester contains at least 10 carbon atoms, and from 0 to about 25% by weight of a fatty acid triglyceride of $C_{8-22}$ fatty acids.

18. The process of claim 13 wherein in step II A) the lipophilic consistency generator is selected from the group consisting of cetyl alcohol, stearyl alcohol, glycerol monostearate, and mixtures of glycerol mono- and distearate.

19. The process of claim 13 wherein in step I A) the liquid oil component consists of from about 50 to 100% by weight of a hydrocarbon oil, from 0 to about 25% by weight of at least one ester of the formulae $$R^1COOR^2$$

$$R^2\text{---}OOC\text{---}R^3\text{---}COOR^2$$

$$R^1\text{---}COO\text{---}R^3\text{---}OOC\text{---}R^1$$

in which $R^1$ and $R^2$ are $C_{1-22}$ alkyl groups or $C_{8-22}$ alkenyl groups and $R^3$ is a $C_{2-16}$ alkylene group, and wherein the ester contains at least 10 carbon atoms, and from 0 to about 25% by weight of a fatty acid triglyceride of $C_{8-22}$ fatty acid;

the nonionic emulsifier in step I B) is an adduct of 8 to 16 mols of ethylene oxide with a saturated $C_{16-22}$ fatty alcohol; and in step II D) the thickened and cooled emulsion has a yield point of from about 10 to about 50 Pascal.

20. The process of claim 13 wherein in step II C) from about 0.01 to about 0.3 parts by weight of the consistency generator is mixed with the emulsion.

21. The process of claim 13 wherein in step II A) the lipophilic consistency generator is selected from the group consisting of cetyl alcohol, stearyl alcohol, glycerol monostearate, and mixtures of glycerol mono- and distearate.

22. The process of claim 13 wherein the oil-in-water emulsion formed in step I A) is a microemulsion.

* * * * *